United States Patent [19]
Gray et al.

[11] Patent Number: 5,624,425
[45] Date of Patent: Apr. 29, 1997

[54] LOCALIZED APPLICATION OF FINE DENIER FIBERS ONTO A SPUNBONDED WEB FOR OPTIMIZATION OF LEG CUFF HYDROPHOBICITY IN DIAPERS AND PADS

[75] Inventors: Brian F. Gray, Burlington; Pietro Cecchetto, Maple, both of Canada

[73] Assignee: The Procter & Gamble Company, Cincinnati, Ohio

[21] Appl. No.: 417,084

[22] Filed: Apr. 5, 1995

[51] Int. Cl.$^6$ .............................. A61F 13/15; A61F 13/20
[52] U.S. Cl. .................. 604/385.2; 604/378; 604/385.1; 604/393; 604/400
[58] Field of Search ............................ 604/358, 370, 604/378, 385.1, 385.2, 393, 400–402

[56] References Cited

U.S. PATENT DOCUMENTS

| | | |
|---|---|---|
| 3,860,003 | 1/1975 | Buell . |
| 3,871,378 | 3/1975 | Duncan et al. . |
| 3,916,900 | 11/1975 | Breyer et al. . |
| 4,040,423 | 8/1977 | Jones, Sr. . |
| 4,324,246 | 4/1982 | Mullane et al. . |
| 4,342,314 | 8/1982 | Radel et al. . |
| 4,374,888 | 2/1983 | Bornslaeger . |
| 4,463,045 | 7/1984 | Ahr et al. . |
| 4,490,148 | 12/1984 | Beckestrom . |
| 4,496,360 | 1/1985 | Joffe et al. . |
| 4,500,316 | 2/1985 | Damico . |
| 4,655,757 | 4/1987 | McFarland et al. . |
| 4,699,622 | 10/1987 | Toussant et al. . |
| 4,704,115 | 11/1987 | Buell . |
| 4,781,966 | 11/1988 | Taylor . |
| 4,806,598 | 2/1989 | Morman . |
| 4,828,556 | 5/1989 | Braun et al. . |
| 5,002,814 | 3/1991 | Knack et al. . |
| 5,069,677 | 12/1991 | Sakurai et al. . |
| 5,108,691 | 4/1992 | Elliott . |
| 5,151,092 | 9/1992 | Buell et al. . |
| 5,152,714 | 10/1992 | Audsley et al. . |
| 5,171,391 | 12/1992 | Chmielewski et al. . |
| 5,180,620 | 1/1993 | Mende . |
| 5,192,606 | 3/1993 | Proxmire et al. ...................... 604/378 |
| 5,221,274 | 6/1993 | Buell et al. . |
| 5,229,191 | 7/1993 | Austin . |
| 5,246,429 | 9/1993 | Poccia et al. . |

*Primary Examiner*—John G. Weiss
*Assistant Examiner*—P. Zuttarelli
*Attorney, Agent, or Firm*—Harness, Dickey & Pierce, P.L.C.

[57] ABSTRACT

A disposable absorbent article that effectively prevents the leakage of body fluids beyond its confines. The article of the present invention comprises a body having a fluid-impermeable backsheet, an intermediate, fluid-absorbing core, and a fluid-permeable topsheet. A pair of leg cuff assemblies is attached to the body. Each assembly comprises a cuff standing portion and a cuff base portion. The assemblies are composed of two hydrophobic nonwoven layers. A first layer is composed of a spunbonded web and a second layer is composed of a meltblown fiber. The first layer extends from the free, unattached end of the cuff standing portion to the distal edge of the article defining the leg opening. The second layer is provided where needed and in weights as needed to provide maximum assembly hydrophobicity with a minimum use of material. This construction allows the cuff assemblies to form fluid-impermeable dams which prevent passage of body fluid beyond the article along its leg hole sides.

24 Claims, 3 Drawing Sheets

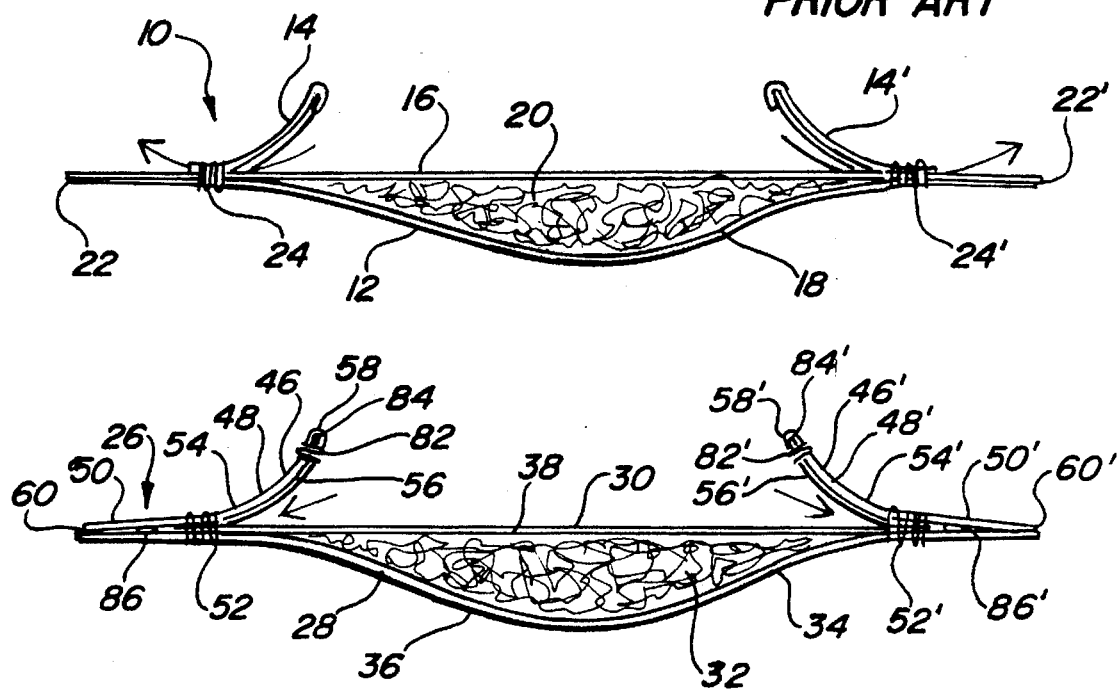
*Fig-1*
PRIOR ART
*Fig-2*
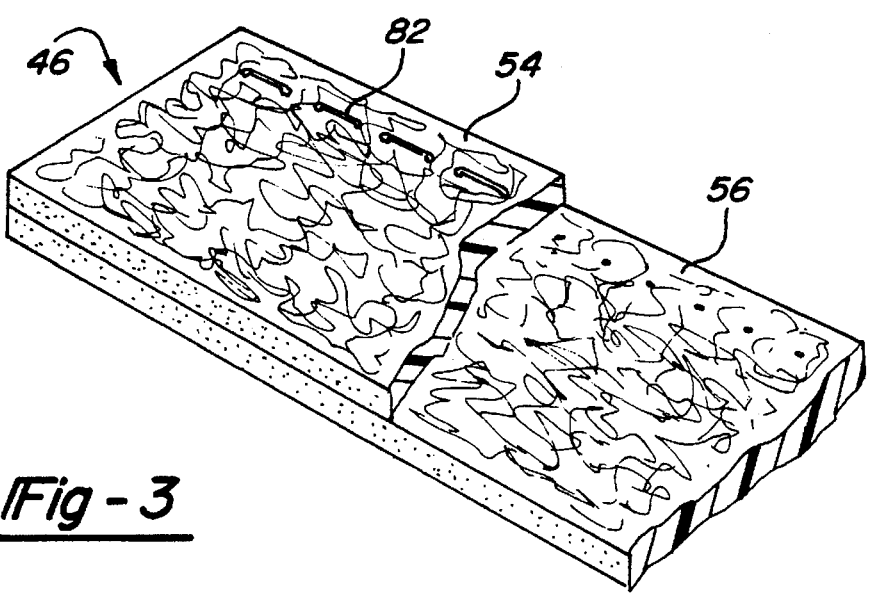
*Fig-3*

LOCALIZED APPLICATION OF FINE DENIER FIBERS ONTO A SPUNBONDED WEB FOR OPTIMIZATION OF LEG CUFF HYDROPHOBICITY IN DIAPERS AND PADS

BACKGROUND OF THE INVENTION

1. Technical Field

This invention relates to materials for absorbent articles, such as disposable diapers, incontinent briefs, and feminine pads. More particularly, this invention relates to the localized use of fine denier fibers, such as meltblown fibers of very low denier, in conjunction with a spunbonded web to maximize hydrophobicity of selected regions of disposable absorbent articles such as diapers, briefs and pads.

The present invention has further relation to the application of a meltblown fiber-spunbonded web combination in the standing cuff region of disposable absorbent articles.

2. Discussion

It has long been known in the art of disposable absorbent articles that it is extremely desirable to construct absorptive devices, such as disposable diapers, incontinent briefs, sanitary pads, and the like, so that leakage of body fluids is prevented. Disposable diapers, incontinent briefs, and sanitary pads are well known articles of manufacture which are respectively worn by infants, incontinent adults, and menstruating women. Diapers and briefs are worn about the lower torso and are intended to absorb and contain urine and feces thereby preventing the urine and feces from soiling, wetting, or otherwise contaminating articles (e.g., clothing and bedding) which come into contact with the wearer. Sanitary pads serve a similar protective function.

In general, disposable absorbent articles all have the same basic structure which comprises an absorbent core encased between a liquid permeable user contacting topsheet and a liquid impermeable backsheet. The prior art, of course, teaches numerous variations of and elements in addition to the basic topsheet, backsheet, and absorbent core arrangement. Many of these improvements are directed to overcoming the problem of side leakage along the thigh of the user. For example, and with particular respect to diapers and briefs, an improvement in the performance of these articles has been achieved by the addition of elastic along the portion of the disposable article which contacts the wearer's thigh thereby providing elasticized leg openings when the article is worn. Exemplary of this improvement is U.S. Pat. No. 3,860,003 issued on Jan. 14, 1975 to Buell for CONTRACTIBLE SIDE PORTIONS FOR DISPOSABLE DIAPER and commonly assigned to the assignee of the instant application.

Experience has taught that while elasticized leg openings improved the control of side leaks, additional barrier protection was necessary. Leg "cuffs" were developed in response to this need. The traditional cuff comprises a strip of fluid-impermeable material that is attached to the body of the article by stitching or by adhesive. When the absorbent article is lying flat or when in its folded state as provided to the consumer, the cuffs generally lie flat adjacent the topsheet. When worn, the cuffs extend perpendicularly with respect to the topsheet to nest in the groins of the wearer from front side to back side, thus wrapping around the crotch area and forming a fluid-impermeable seal. Instead of leaking out of the absorbent article and along the wearer's thigh, body fluid is supposed to be retained within the confines of the area formed between the generally parallel fluid-impermeable cuffs and the fluid-impermeable backsheet.

While some of the problems of providing leakage resistant waste containment garments have been at least partially ameliorated by previously-disclosed garments, none has solved the problems in the manner or to the extent of the present invention. Specifically, there is known in absorbent articles of the prior art a tendency for flowing, non-absorbed liquids to pass under the attachment seam formed where the cuff is hinged to the body of the absorbent article.

In addition to known cuffs allowing leakage, these cuffs are typically composed of materials that are either insufficiently hydrophobic, are resistant to the passage of air and hence do not "breathe" (typical of conventional nonwoven laminates) or are too costly to be used in mass production. Furthermore, certain types of known cuffs are not composed of material which is particularly soft to the touch, thus making the cuffed article unpleasant to wear.

It is clear that known disposable absorbent articles have generally failed to overcome the problem of side leakage.

It is therefore an object of the present invention to overcome the disadvantages associated with known absorbent articles by providing a disposable absorbent article that effectively resists the passage of body fluids beyond its confines.

It is a further object of the present invention to provide a cuff assembly that is composed of at least two nonwoven layers of material to provide maximum hydrophobicity.

Still another object of the present invention is to combine meltblown and spunbonded polymers to provide ranges of hydrophobicity in a cost optimized manner to meet the specific physical property needs as required for different regions across the width of the cuff assembly.

Still a further object is to provide cuff assemblies composed of combined spunbonded and meltblown fibers demonstrating superior hydrophobicity to conventional spunbonded or carded materials of similar weights.

Another object of the present invention is to provide cuff assemblies that demonstrate superior resistance to loss of hydrostatic head due to manipulation as compared with conventional spunbonded or carded materials or non-optimized multidenier materials.

Yet a further object of the present invention is to provide cuff assemblies that allow for the transmission of air while retaining hydrophobic properties. This "breathable" characteristic makes articles constructed according to the following design more comfortable to wear.

SUMMARY OF THE INVENTION

The present invention achieves these objectives in an improved disposable absorbent article that comprises a body having a fluid-impermeable backsheet, an absorbent core, and a fluid-permeable topsheet. Attached to the body are a pair of cuff assemblies. Each of the cuff assemblies includes an axially aligned cuff standing portion and a cuff base portion joined to the standing portion at a hinge.

The cuff assembly is preferably composed of two layers of nonwoven hydrophobic material. The upper or skin contacting layer is composed of a spunbonded web. The lower or topsheet facing layer is composed of meltblown fibers. The design of the cuff assembly can be tailored to specific and varying hydrophobicity requirements across its width by the localized application of meltblown fibers of very low denier, thereby providing hydrophobicity only where required while still retaining a high degree of breathability.

Each cuff base portion is adhered to the top of the body of the absorbent article while the cuff standing portions are hinged along substantially parallel seams. The upper layer of the cuff assembly is a continuous sheet that extends laterally from the free, unattached end of the cuff standing portion outward to the distal edge defining the leg hole side of the article. By this construction, the cuff assemblies form fluid-impermeable dams which prevent passage of body fluid beyond the article along its leg hole sides.

Other objects and advantages of the present invention will be made apparent as the description progresses.

BRIEF DESCRIPTION OF THE DRAWINGS

The various advantages of the present invention will become apparent to one skilled in the art by reading the following specification and appended claims and by referencing the following drawings in which:

FIG. 1 is a cross-sectional view of an example of an absorbent article of the prior art;

FIG. 2 is a cross-sectional view illustrating the absorbent article of the present invention;

FIG. 3 is a schematic perspective view of a section of the two layer nonwoven fabric of the present invention for use in the cuff assemblies shown partially broken away;

DETAILED DESCRIPTION OF THE PREFERRED EMBODIMENT

Figure 4:
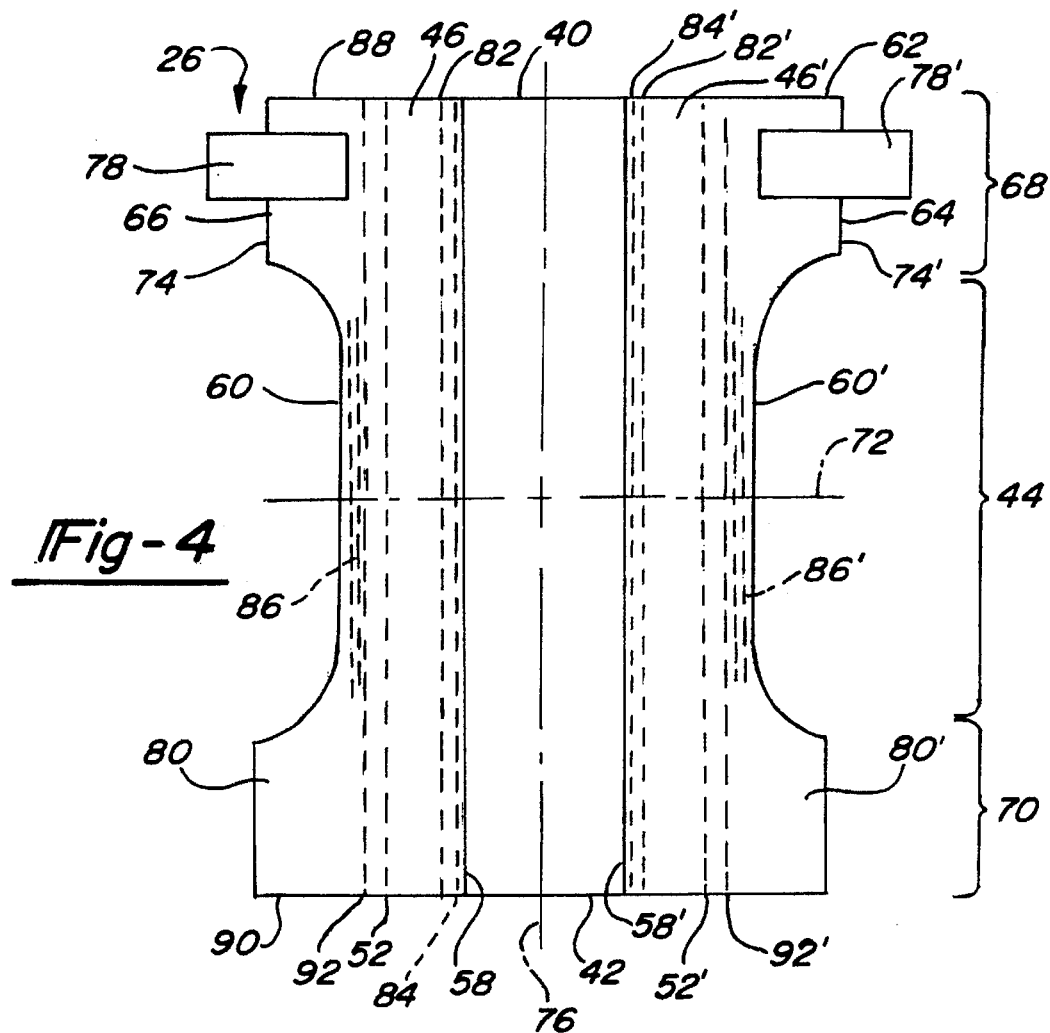
FIG. 4 is a plan view of the inner side of a diaper according to the present invention.

There is shown in the drawings a preferred embodiment of the present invention as it would be used in a disposable absorbent article and, in particular, in a disposable diaper for use by infants and toddlers. As used herein, "disposable absorbent article" refers to articles which are intended to absorb and contain liquids such as those discharged from the human body (e.g., blood, menses, urine, stool) and, further, to articles which are intended to be discarded after a single use (i.e., they are not intended to be laundered and stored or otherwise reused). It should be understood, however, that the present invention is also applicable for use in other disposable articles such as incontinent briefs for adults and catamenial pads. While the preferred absorbent article described herein is a disposable diaper, a detailed description of the general construction of sanitary napkins and suitable materials for use therein is found in U.S. Pat. No. 3,871,378, issued to Duncan and Smith on Mar. 18, 1975, the disclosure of which is incorporated herein by reference. By incorporating cuff assemblies of the present invention with the disclosure of that patent, an absorbent sanitary napkin having many of the preferred characteristics of the below-described diaper may be achieved.

As is well known, the disposable diaper is an absorbent article worn by infants and toddlers external to the urogenital region and circumscribing the crotch area of the lower and of the torso which is intended to absorb and contain urine and stool.

FIG. 1 is a cross-sectional view of an example of an absorbent article of the prior art, generally illustrated as 10. The prior art article 10 comprises a generally longitudinal article body 12 and a pair of leg cuffs 14, 14' attached to the body 12. The body 12 of the article 10 basically comprises a fluid-permeable topsheet 16, a fluid-impermeable backsheet 18, and an intermediate absorbent core 20. A pair of distal edges 22, 22' define the sides of the article 10 which are positioned adjacent the user's upper inner thighs when the article 10 is worn.

The leg cuffs 14, 14' are conventionally composed of a hydrophobic material. This construction is intended to create a wall through which body fluid is not supposed to pass. According to known techniques, the cuffs 14, 14' are stitched, glued, or are heat-welded to the body 12 of the article 10 along generally parallel attachment seams 24, 24' that are spaced apart from the distal edges 22, 22'. The cuffs 14, 14' may be composed of a single layer of material, or may be composed of multiple layers. In their multiple layer construction, known cuffs comprise materials laminated to one another with an adhesive to hold the layers together. While more or less blocking the passage of fluid, these laminated cuffs also prevent the transmission of drying air and do not provide for any degree of breathability.

The failure of the prior art to provide a satisfactory barrier to the free flow of body fluids over the distal edges 22, 22' and along the user's legs (not shown) lies in the construction involving the attachment seams 24, 24'. While the hydrophobic character of the cuffs 14, 14' directs fluid to the absorbent core 20 for the most part, a significant amount of free-flowing fluid passes between the cuffs 14, 14' and the body 12 along the seams 24, 24', as illustrated by the arrows. This is particularly true where the absorbent core 20 is at or is near its saturation point.

FIG. 2 is a cross-sectional view of an absorbent article of the present invention, generally illustrated as 26, which overcomes the disadvantages inherent in known absorbent articles, of which the article 10 is a sample. The article 26 includes a body 28 consisting of a fluid-permeable topsheet 30, an absorbent core 32 having a central area that defines a crotch zone, generally indicated by "Z", and a fluid-impermeable backsheet 34. The fluid-permeable topsheet 30 functions essentially as a oneway medium through which body fluids pass to the absorbent core 32, thereby keeping the skin of the wearer dry and comfortable. While a preferred configuration of the absorbent article 26 is shown, the article 26 can have a number of well known configurations. Exemplary configurations are described generally in: U.S. Pat. No. 3,860,003 issued to Buell on Apr. 18, 1989; U.S. Pat. No. 5,151,092 issued to Buell et al. on Sep. 29, 1992; and U.S. Pat. No. 5,221,274 issued to Buell et al. on Jun. 22, 1993. Each of these patents is incorporated herein by reference. Another configuration to which the present invention can be readily adapted is described in U.S. patent application Ser. No. 08/203,456; field on Feb. 28, 1994 in the name of Roe et al. and incorporated herein by reference.

The absorbent core 32 has first and second opposed faces 36 and 38, respectively. The backsheet 34 overlays the first opposed face 36 and is in contact with the user's clothes (not shown). The topsheet 30 overlays the second opposed face 38 and is placed against the user's body when the article 26 is worn.

The topsheet 30 is a soft barrier film and is preferably composed of a hydrophobic resilient plastic webbing. It may be made from any of the materials conventional for this type of use. Suitable materials are described in U.S. Pat. No. 4,342,314, issued to Radel and Thompson on Aug. 3, 1982 and U.S. Pat. No. 4,463,045, issued to Ahr, Louis, Mullane and Ouellette on Jul. 31, 1994, both of which patents are incorporated herein by reference. The topsheet 30 gives the wearer a feeling of dryness by funneling moisture away from the wearer. The topsheet 30 is also soft to the touch.

A number of manufacturing techniques can be used to manufacture the topsheet 30. For example, the topsheet 30 may be woven, nonwoven, spunbonded, carded, or the like. A preferred topsheet 30 is carded and thermally bonded by means well known to those skilled in the nonwoven fabrics art. Preferably the topsheet 30 has a weight of from about 18 to 25 grams per square yard, and has a minimum dry tensile strength of at least about 400 grams per centimeter in the machine direction and a wet tensile strength of at least about 55 grams per centimeter in the cross machine direction.

The absorbent core 32 is composed of any absorbent, hydrophilic fiber and is intended to absorb and contain liquid. It may be manufactured in a wide variety of sizes and shapes (e.g., rectangular or hourglass). While the type of hydrophilic fiber material is not critical for use in the structures of the present invention, any type of hydrophilic fiber which is suitable for use in conventional absorbent products is also suitable for use in the absorbent structures herein. Examples of hydrophilic fiber material include cellulose, modified cellulose, rayon, polyesters such as polyethylene terephthalate (DACRON [trademark]), hydrophilic nylon (HYDROFIL [trademark]), and the like. Other liquid absorbing materials may also be used in the manufacture of the absorbent core 32 such as a multiplicity of plies of creped cellulose wadding, absorbent gelling material, absorbent foams or sponges, or any equivalent material or combination of materials. The total absorbent capacity of the absorbent core 32 should, however, be compatible with the intended use of the disposable absorbent article 26. Further, the size and absorbent capacity of the absorbent core 32 may be varied to accommodate wearers ranging from infants through adults.

The preferred embodiment of absorbent article 26 illustrated in the FIGS. 4 through 6 and discussed below in conjunction therewith has an hourglass shaped absorbent core 32, and is intended to be worn by infants ranging in weight from about 12 to about 35 pounds (about 5 kgs to about 16 kgs). The absorbent core 32 is, therefore, a batt of airfelt approximately 16 inches (about 41 cm) long when measured along the longitudinal centerline, approximately 7 inches (about 18 cm) across first and second ends 40 and 42, and approximately 4 inches (about 10 cm) across the narrowest part of a crotch portion 44. The absorptive capacity of the airfelt used for the absorbent core 32 is sufficient to absorb and retain from about 8 g to 16 g of liquid per gram of absorbent material. Accordingly, the airfelt used in the preferred embodiment shown in FIGS. 4 through 6 weighs from about 30 g to about 70 g and has a generally uniform caliper. It should be understood, however, that the size, shape, configuration, and total absorbent capacity of the absorbent core 32 may be varied (for example, the absorbent core 32 may have a varying caliper, or a hydrophilic gradient, or may contain absorbent gelling materials).

Still with respect to FIG. 2, the backsheet 34 is impervious to liquids and prevents liquids absorbed by the absorbent core 32 from wetting the undergarments, clothing, bedding, and other object which contact the wearer of the disposable article 26. Preferably the backsheet 34 is a polyethylene film of from about 0.0005 to about 0.002 inches thick (about 0.012 to about 0.051 mm), although other flexible, fluid-impermeable materials may also be used. As used herein, the term "flexible" refers to materials which are compliant and which readily conform to the shape and contours of the human body. While any polymerized barrier film may be used as the backsheet 34, a suitable polyethylene film is manufactured by Monsanto Chemical Company and marketed in the trade as Film No. 8020.

In the preferred embodiment of the present invention, the inner surface of the topsheet 30 is secured in contacting relation to the absorbent core 32. This contacting relationship results in liquid penetrating the topsheet 30 faster than if it were not in contact with the core 32. The topsheet 30 can be maintained in contact with the core 32 by applying adhesive, preferably in spaced, limited areas, to the inner surface of the topsheet 30. Examples of suitable adhesives used for this purpose include the acrylic emulsive E-1833BT manufactured by Rohm and Haas Company of Philadelphia, Pa. and the acrylic emulsive WB3805 manufactured by H. B. Fuller Company of St. Paul, Minn. The adhesives can be applied by any of the common techniques well-known to those skilled in the art. For example, the adhesive can be applied by spraying, by padding, or by the use of transfer rolls.

The absorbent core 32 is affixed to the backsheet 34 by any means as is well known in the art of absorbent articles. For example, the absorbent core 32 may be secured to the backsheet 34 by a uniform continuous layer of adhesive, a patterned layer of adhesive, or an array of lines or spots of adhesive.

A pair of hydrophobic cuff assemblies 46, 46' are provided. As is the case with many parts of the present invention, these two components are mirror images of each other. Accordingly, and to avoid unnecessary confusion, generally just one of any two like components of the invention will be discussed, although both the discussed component as well as its counterpart are shown in the several figures, with the latter being identified by its being primed. It is to be understood that discussion of the one will apply equally to the primed component not discussed.

The cuff assembly 46 comprises a cuff standing portion 48 and a cuff base portion 50. The cuff standing portion 48 is generally parallel with its cuff standing portion counterpart 48'. The cuff standing portion 48 is made distinct from the cuff base portion 50 and is hinged thereto by a seam 52. Again, the seam 52 is generally parallel with its counterpart 52'. The cuff assembly 46 is composed of at least one layer of material and could be composed of many layers of material. However, the assembly 46 preferably comprises two layers, as will be described more fully below. As illustrated, the cuff assembly 46 is composed of a first layer 54 and a second layer 56.

The cuff assembly 46 further includes a free, unattached end 58 (as part of the cuff standing portion 48) and a leg opening edge 60 (as part of the cuff base portion 50). The first layer 54 is preferably continuous from the free end 58 to the leg opening edge 60. The second layer 56 may also be continuous to the leg opening edge 60 from the free end 58, but this should not be necessary to eliminate leakage and, for cost reasons, is not preferred. Accordingly, in an alternative embodiment (not shown), only the second layer 56 is continuous between the leg opening edge 60 and the free end 58, while the first layer 54 only partially overlaps the second layer 56.

The topsheet 30 extends at least from the seam 52 to the seam 52'. While it is optional to have the topsheet extend from the edge 60 to the edge 60', this is not necessary, as the first layers 54, 54' of the cuff assemblies 46, 46' provide necessary support. Beyond the seams 52, 52', the first layer 54 is bonded to the first opposed face 36 of the backsheet 34 continuous to the edges 60, 60'.

The seam 52 is created by methods including chemical and thermal adhesive or stitching. A hot melt adhesive such as marketed by Eastman Chemical Products Company of Kingsport, Tennessee under the tradename of Eastbond A-3. As illustrated by the arrows, body fluid is directed by the cuff assemblies 46, 46' toward the absorbent core 32. The cuff assemblies 46, 46', in combination with the backsheet 34, form a fluid-tight pouch in which all body fluid from the urogenital region is captured and held until the article 26 is changed for a fresh one. The enveloping characteristics of the article 26 are more clearly seen and understood with reference to FIG. 6, discussed below.

As noted, each of the cuff assemblies 46, 46' is preferably composed of two layers, although a greater or lesser number may be used. This layered construction is shown in FIG. 3, which illustrates a schematic perspective view of the preferred two layers of the cuff assembly 46.

The first layer 54 of the cuff assembly 46 is composed of a nonwoven web, preferably of the spunbonded type. The web of the first layer 54 preferably has a weight of about 14 g/m$^2$. In spunbonded material, fibers and web are made simultaneously from bulk polymer such as polypropylene, polyethylene, polyester, and nylon, which is melted, then extruded through a linear or circular spinnerette. (At one time spunbonded polyester [17 g/m$^2$] was the material of choice for diaper coverstock, but this has been largely supplanted by an equivalent weight spunbonded polypropylene.) The extruded polymer streams are rapidly cooled and are attenuated (to orient the molecular chains of the fibers so that fiber strength is increased and extensibility is decreased) by air or mechanical drafting rollers to form desired diameter filaments. The filaments are then laid down onto a conveyor belt to form a web having a loft of about 5 inches (about 13 mm). The web is then thermally bonded by a high caloric transfer mechanism (HCTM) process to form a spunbonded web of low crimp filaments having a textile-like diameter range of about 1.7 dtex (1.5 den) or somewhat higher, with a common range being between 1.5–20.0 dtex (1.36–18.0 den). The filaments are bonded by hot embossing.

The second layer 56 is preferably composed of meltblown fibers. As known to those skilled in the art, the meltblown process results in the extrusion of a thermoplastic, fiber-forming polymer through a linear die containing from about 20 to about 40 small orifices per inch (or 2.54 cm) of die width having a diameter of from $1.0 \times 10^{-2}$ inch ($25.0 \times 10^{-2}$ mm) to about $3.0 \times 10^{-2}$ inch ($76.2 \times 10^{-2}$ mm). Convergent streams of hot air rapidly alternate the extruded polymer streams to form filaments. The alternated filaments are then blown by high velocity air onto a collector screen, thus forming a meltblown web. This process produces a web comprising filaments that are much smaller in diameter than those of typical textile fibers (typically less than 1 um).

An amount of fiber fusion bonding occurs during the actual web formation. However, this bonding is inadequate to provide correct tensile characteristics, so hot embossing is often used to enhance strength. (To create a bonding pattern in the web, ultrasonic energy with pressure may be used to generate the necessary heat.) The final product strength is still not high, but as the meltblown second layer 56 is provided in conjunction with the stronger spunbonded first layer 54, strength of the meltblown material is not a critical factor. Because of its fine capillary network, meltblown fibers treated with moisture repellant demonstrate good moisture-barrier properties.

Bulk polymers commonly used for the meltblowing process include primarily polypropylene, although polyethylene, nylon, and polyesters may be used. Because the filaments of the web are nonuniform, they cannot be described in terms of decitex or denier.

Placement of the spunbonded first layer 54 over the second layer 56 provides at least three advantages. First, the spunbonded first layer 54 protects the meltblown second layer from abrasion. This is a concern because excessive manipulation of the meltblown fibers may result in either their "wetting out" wherein hydrophobicity is effectively lost or in their removal due to simple abrasion. Second, this array places the softer, more compliant spunbonded layer in contact with the user's skin. Third, and perhaps most importantly, the combination of the two layers according to the present invention without lamination with adhesives provides a cuff design that not only resists moisture transmission at least as well as the laminated cuffs of the prior art, but also provides the benefit of air transmission or breathability which known laminated cuffs fail to provide.

The strategic and localized combination of meltblown and spunbonded materials can significantly increase the hydrophobicity of a single nonwoven material, and this is particularly true when the denier and pore size (the three-dimensional spaces between strands of meltblown as measured by a parameter) are optimized, as in the invention of the present application.

Two considerations are important with respect to pore configuration. First, it is desired that the individual pores be as perfectly circular as possible. Second, it is desired that the pores be uniformly sized. The latter characteristic is important in that in a field of pores having a relatively similar pore size, only a few pores of larger-than-average size can destroy impermeability. Pore sizes may be regulated by controlling conditions during the lay-down of the meltblown on the non-woven forming bed such as vacuum draw, polymer flow rate, and the gap between the spinnerette and the forming belt.

Beyond the use of the spunbonded and meltblown layers toward providing a general improvement of hydrophobicity by their mere combination, hydrophobicities (static head measurements) can be still further improved by adjusting weights of the layers. The following Table illustrates hydrophobicity data based on various cuff materials and weights (in g/m$^2$) and demonstrates how meltblown and spunbonded components can be combined in selected ratios so as to meet both hydrophobicity and strength requirements.

TABLE

| | STATIC HYDROPHOBICITY DATA | | | | |
|---|---|---|---|---|---|
| MATERIALS | 10 g Meltblown 14 g Spunbond Soft Pattern (improved meltblown) | 12 g Meltblown 14 g Spunbond (improved meltblown) | 14 g Meltblown 14 g Spunbond (improved meltblown) | 6 g Meltblown 14 g Spunbond | 25 g Spunbond |
| HYDROPHOBICITY (mm water) | 210 | 250 | 300 | 80 | 40 |

With reference to the Table, it is generally notable that the hydrophobicities of multidenier materials in which spunbonded and meltblown materials are combined are significantly higher than that of pure spunbonded material alone.

The Table also illustrates the advantages of using improved or optimized meltblown fibers in which the pore size and uniformity was optimized. This is best understood by comparing the hydrophobicity of the unimproved 6 g/m² meltblown—14 g/m² spunbonded combination with the optimized, improved meltblown-spunbonded combinations. In each instance the latter results far exceed the former.

Optimization of the meltblown layer is achieved by careful regulation of operating conditions such as air temperature ranges (normally between 260 to 480 degrees C.) and flow rates (normally between 1.4–7.0 kg/min per cm²) of the heated bulk polymer and by controlling the orientation of the fibers during the preparation of the web. Improved web uniformity, pore size (which is normally very small) and denier within the meltblown layer is critical in maximizing hydrophobicity.

The Table specifically illustrates how combinations of spunbonded and meltblown layers of different weights can be used to maximize hydrophobicity. The first three columns represent spunbonded-meltblown combinations in which the meltblown web is optimized. As illustrated, a very high degree of hydrophobicity is achieved in the instance where the spunbonded layer has a weight of 14 g/m² and the meltblown layer has the same weight. However, it is important to note that maximum hydrophobicity is not necessarily a product of these weights exclusively. Hydrophobicity according to the present invention is a function of the weight of the meltblown layer. This relationship is not, however, infinitely linear, in that at a certain point each additional gram of meltblown provides a decreasing probability of stopping a leak. However, within the feasible weight range according to known techniques, additional weight of meltblown does provide improved hydrophobicity, as illustrated in the Table.

Furthermore, while the illustrated combination of 14 g/m² meltblown and 14 g/m² spunbond suggests highest hydrophobicity, this is not necessarily the case, in that, theoretically, the combination of 16 g/m² meltblown and 14 g/m² spunbond could have a hydrophobicity of 350 mm. However, the 14 g/m² meltblown—14 g/m² spunbond ratio is the preferred combination for at least three reasons. First, there is the economic consideration. To add, for example, two grams to the meltblown layer would require subtracting two and one-half to three grams from the spunbonded layer, because meltblown material is more costly than spunbonded material. This trade-off is not justifiable given the relatively small improvement realized in hydrophobicity.

Second, a hydrophobicity greater than 300 millimeter is not necessary. In general, there are two modes of diaper failure, and they are failure due to insufficient resistance to fluid transfer (static head) and failure caused by manipulation of the material. With respect to static fluid resistance, a hydrophobicity of 300 millimeters is more than adequate to contain the fluid, excluding the effects of manipulation. With respect to manipulation, applicants have found that the 14 g/m² meltblown—14 g/m² spunbond ratio provides more than adequate resistance to the effects of manipulation. Accordingly, the 14 g/m² meltblown—14 g/m² spunbond ratio provides a matrix that is resistant to both modes of failure.

Third, there is the practical concern of product availability. Spunbonded material of weights such as 12 g/m² and 14 g/m² are readily available according to current supply. Therefore, while the present invention should not be limited to the 14 g/m² meltblown—14 g/m² spunbond combination, this is the preferred ratio. When a meltblown layer having a lesser weight is used, hydrophobicity declines.

In addition to achieving improved hydrophobicity through optimization set forth above, the optimized meltblown layer, when combined with a spunbonded layer, also demonstrates retention of more of its barrier properties even when physically manipulated. Experimentation shows that non-optimized multideniers and treated or untreated carded webs tend to fail catastrophically when manipulated. For example, it has been noted that a stream of liquid passes easily at the region which has been manipulated.

Beyond the use of preferred weights of materials in preferred combinations, the strategic use of materials and selected weights in selected areas on the disposable absorbent article 26 further maximizes fluid retention while minimizing manufacturing costs as discussed below.

Figure 5:
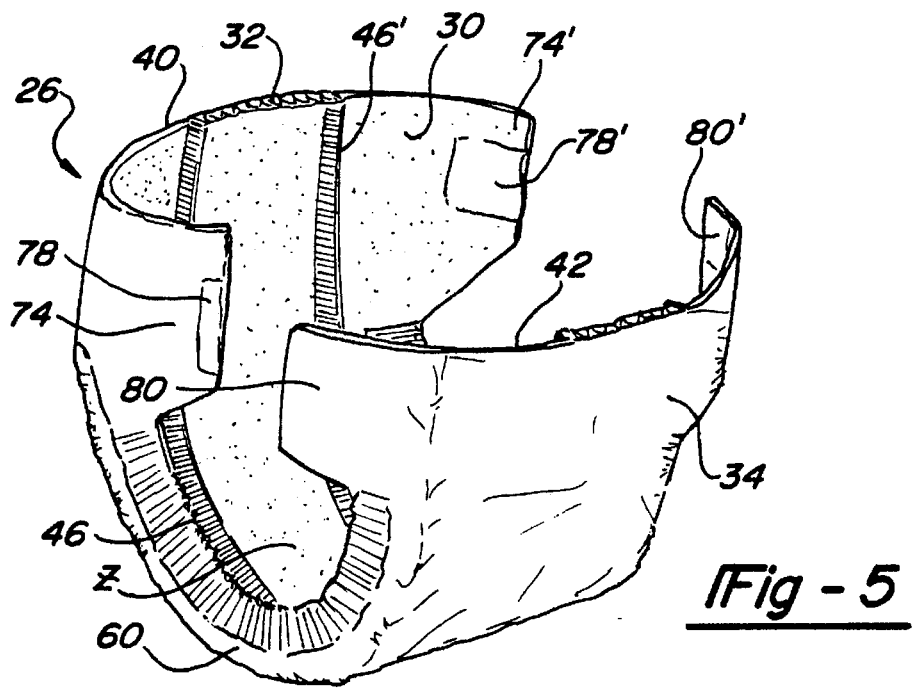
FIG. 5 is a perspective view of the disposable absorbent article of the present invention in the unfolded condition.

FIG. 4 is a plan view of the absorbent article 26 of the present invention viewed from its inner side and showing the article 26 prior to its being folded and placed on the wearer. The article 26 includes a periphery 62 that defines the article's outer periphery or outer extent. The periphery 62 comprises the first end 40, the second end 42, a first longitudinal side 64, and a second longitudinal side 66. The article 26 has first and second waist portions 68 and 70 extending, respectively, from the first end 40 and the second end 42 of the article periphery 62 toward the lateral centerline 72 of the article 26 a distance from about 1/5 to 1/3 the length of the article. The waist portions 68 and 70 comprise those portions of the article 26 which, when worn, encircle the waist of the wearer. The crotch portion 44 is that portion of the article 26 between the first and second waist portions 68 and 70, and comprises that portion of the article 26 which, when worn, is positioned between the legs of the wearer and covers much of the lower torso of the wearer.

The first waist portion 68 includes a pair of opposed back ears 74, 74' that extend laterally outward from the longitudinal centerline 76. Adhesive fasteners 78, 78' are provided on the back ears 74, 74' and include a backing sheet and a releasable adhesive tape, as is well known in the art. The second waist portion 70 includes a pair of opposed front ears 80, 80' that extend laterally outward from the longitudinal centerline 76. The front ears 80, 80' are those portions of the second waist portion 70 which are overlain by the first waist portion 68 when the article 26 is fastened about the waist of the wearer. The extent to which the second waist portion 70 is overlain will depend on the overall dimensions and shape of the article 26 and the size of the wearer. Releasable attachment of the first waist portion 68 with the second waist portion 70 is accomplished by selective use of the fasteners 78, 78'.

When the article 26 is held flat upon a surface, the cuff standing portion 48 lies against the topsheet 30, as illustrated in FIG. 4. With respect to that figure, a seam 82, shown in broken lines, is provided to hem the overfolded end of the cuff standing portion 48 against its backside, (also as illustrated in cross-section in FIG. 2). (The seam is formed through chemical adhesive, thermal bonding, or stitching.) Within the hemmed area is an elastomeric band 84, shown in broken lines (again seen in cross-section FIG. 2), which causes the cuff standing portion 48 to extend perpendicularly outwardly from the body of the article 26 when in the arcuate shape formed when the article is worn, as illustrated in FIG. 5.

The seam 52, as discussed above with respect to FIG. 2 and illustrated in FIG. 4 in broken lines, defines the hinging point at which the cuff standing portion 48 is distinguishable from the cuff base portion 50. Like the seam 82, the seam 52 is formed through chemical adhesion, thermal bonding, or mechanical stitching. An elastomeric strip 86, shown in broken lines, provides elasticity along the leg opening so that the strips tend to draw and hold the article 26 against the legs of the wearer.

The spunbonded first layer 54 extends from the free, unattached end 58 of the cuff standing portion 48 to the leg opening edge 60. In addition, the first layer 54 also extends laterally from the free, unattached end 58 of the cuff standing portion 48 to the back ear 74 and to the front ear 80. The first layer 54 also extends axially from a back end edge 88 to a front end edge 90. For the most part, the first layer 54 is bonded directly to the backsheet 34. This is mostly the case at the back ear 74 and at the front ear 80. The only portion of the inner side of the article 26 not covered by the spunbonded layer is the topsheet 30 exposed between the seams 52, 52'.

In addition, the spunbonded first layer 54 may be modified to make it more or less three dimensional. A more three dimensional construction will give greater thickness and resiliency to the spunbonded layer. The thicker embodiment would reduce the strain on the meltblown layer when the spunbonded layer itself is subjected to manipulation during use. A more open or lofty spunbonded structure would provide this benefit more cost effectively than would spunbonded webs of higher base weights.

The meltblown second layer 56 also extends from the free, unattached end 58 of the cuff standing portion 48, but preferably terminates only beyond the seam 52 at about a termination area 92, shown approximately as a broken line. This selective application of the meltblown layer provides maximum hydrophobicity directly to the area most exposed to body fluids, the cuff standing portion 48 and the associated seam 52. This is the ideal construction whereby meltblown fibers are provided beyond this region only as needed so as to meet structural demands. In addition, at the back ear 74 and at the front ear 80 the spunbonded first layer 54 is preferably left without being coated with meltblown fibers at all in order to create varying physical properties across the web by specifically providing areas of available strain suitable for application in sidestretch products.

Conversely, it is possible that the meltblown fiber coating be applied to the entire underside of the first layer 54. However, to enhance the cost effectiveness of the construction of the present invention and to maximize the use of the fiber, only as much of the meltblown second layer 56 beyond the cuff assembly 46 is used so as to meet structural demands. Furthermore, low levels of meltblown material may be used in the amount of between, for example, 1 g/m$^2$ and 4 g/m$^2$ near the free end 58 to prevent adhesive glue penetration or to reduce the appearance of their spots in the web, thereby increasing the apparent level of uniformity. This amount is reduced from the preferred weight of between 10 g/m$^2$ and 14 g/m$^2$ in the cuff standing portion 48. Of course, the denier and location of the meltblown material may be modified across the web as needed.

The spunbonded first layer 54 and the meltblown second layer 56 are preferably laminated with an adhesive to prevent wicking action towards bond sites and to improve overall hydrophobicity and resistance to abrasion. Alternatively, the first layer 54 and the meltblown second layer 56 may have a heat-sensitive adhesive layer (incorporating an elastomer such as ethylene-vinyl acetate copolymer [EVA] for improved adhesion) provided between the layers. All of the layers are thereafter bonded by thermal bonding in a hot-melt process. Either embodiment provides a multilayered construction that demonstrates high degrees of both hydrophobicity and breathability.

As mentioned previously, FIG. 5 is a perspective view of the disposable absorbent article 26 of the present invention in its unfolded condition. As may be seen, the cuff standing portions 48, 48' extend perpendicularly from the body of the article 26 when positioned in this arcuate, worn configuration.

Figure 6:
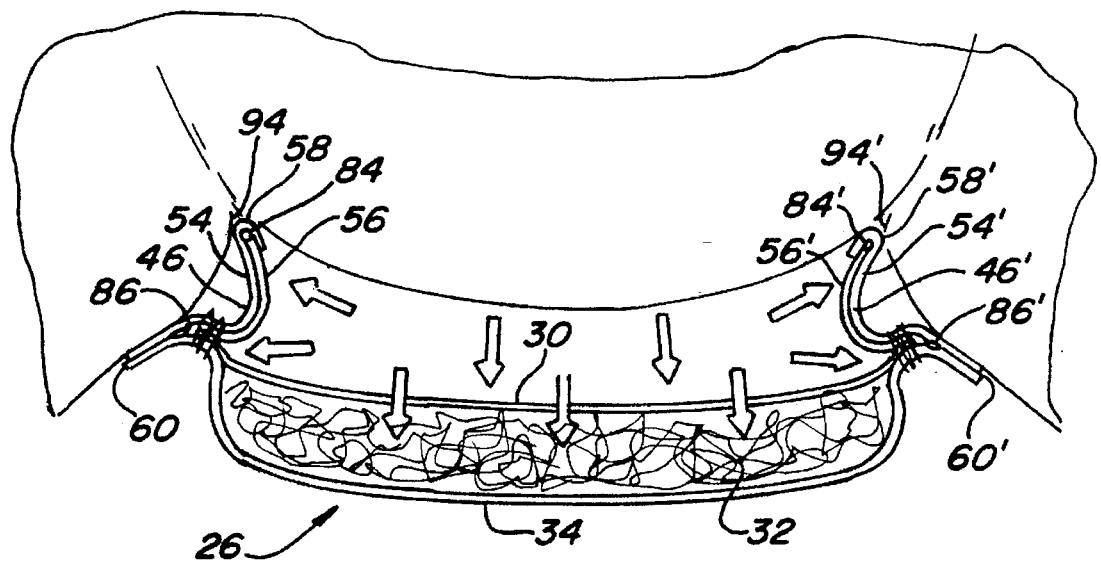
FIG. 6 is a fragmentary coronal view of an individual and the disposable absorbent article of the present invention in place as worn.

FIG. 6 is a fragmentary coronal view of an individual and the disposable absorbent article 26 of the present invention positioned in place as worn. (A coronal view is the frontal plane that passes through the long axis of the body.) When the article 26 is worn, the elastomeric band 84 of the cuff standing portion 48 generates an upward force, that is, against the body, due to the energy in the elastic and the fit of the article 26. The free ends 58, 58' of the cuff standing portions 48, 48' are snugly fitted into the groins 94, 94' of the body. This results in a gasket-like seal being formed between the free ends 58, 58' and the body, thus maintaining body fluid in the crotch area and redirecting fluid back to the absorbent article 26 for absorption. The hydrophobic cuff end-to-leg edge construction of the present invention prevents bypassage of body fluid beyond the groins 94, 94' of the wearer.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

We claim:

1. In a body fluid absorptive article, said article including:
   a longitudinal body, said body having a long axis, said body including an absorbent core consisting of a central crotch zone having two opposed sides extending outwardly from each side of said crotch zone, each of said sides having a distal edge defining a leg opening, said crotch zone defining means for positioning adjacent the crotch of the wearer to absorb body fluids, said absorbent core being composed of fluid-absorbent material, said body further including a fluid-permeable topsheet and a fluid-impermeable backsheet, said fluid-absorbent material of said absorbent core being disposed between said topsheet and said backsheet; and
   a pair of cuff assemblies, each of said pair of cuff assemblies including a cuff standing portion for fitting substantially within the groins of the wearer's crotch area and a cuff base portion for attachment to said longitudinal body, said cuff standing portion having a free end, each of said cuff assemblies having a first layer and a second layer, one of said layers extending from said free end of said cuff standing portion to said distal edge of said body and the other of said layers extending from said cuff standing portion and terminating between said cuff base portion and said distal edge of said body.

2. The body fluid absorptive article of claim 1, wherein said first layer extends from said free end of said cuff standing portion to said cuff base portion.

3. The body fluid absorptive article of claim 1, wherein said second layer extends from said free end of said cuff standing portion to said cuff base portion.

4. The body fluid absorptive article of claim 1, wherein said first layer is composed of a spunbonded material.

5. The body fluid absorptive article of claim 1, wherein said second layer has a material weight, said material weight of said second layer being reduced proximate said free end of said cuff standing portion relative to the remainder of said cuff standing portion.

6. The body fluid absorptive article of claim 5, wherein said weight of said second layer proximate said free end of said cuff standing portion is between 1 g/m$^2$ and 4 g/m$^2$.

7. The body fluid absorptive article of claim 5, wherein said weight of said cuff standing portion other than proximate said free end of said cuff standing portion is between 10 g/m$^2$ and 14 g/m$^2$.

8. The body fluid absorptive article of claim 1, wherein said second layer is composed of a meltblown material.

9. The body fluid absorptive article of claim 1, wherein said first layer has a material weight and said second layer has a material weight, said weight of said first layer being substantially the same as said weight of said second layer.

10. The body fluid absorptive article of claim 1, wherein said first layer has a material weight and said second layer has a material weight, said weight of said first layer being about 14 g/m$^2$ and said weight of said second layer being in the range of between about 10 g/m$^2$ and about 14 g/m$^2$.

11. The body fluid absorptive article of claim 1, wherein said article is a diaper.

12. A pair of laminated cuff assemblies having regions of relatively low and high hydrophobicities for attachment to an absorbent article in which said article has an absorption region and a pair of opposed leg edges, each of said assemblies comprising a cuff standing portion and a cuff base portion, the cuff portions aiding in the prevention of the leakage of body fluids beyond the leg edges of the absorbent article, each of said assemblies comprising:

a first layer which is a nonwoven web having a first side and a second side;

a second layer joined to said second side of said first layer, said second layer comprising a second nonwoven web, said second layer having a region of relatively light weight and a region of relatively heavy weight whereby said region of light weight has relatively low hydrophobicity and said region of heavy weight has relatively high hydrophobicity.

13. The laminated assemblies of claim 12, in which said first layer is composed of a spunbonded web.

14. The laminated assemblies of claim 12, in which said second layer is composed of a meltblown web.

15. The laminated assemblies of claim 14, in which said region of light weight has a weight range of between 1 g/m$^2$ and 4 g/m$^2$.

16. The laminated assemblies of claim 15, in which said region of heavy weight has a weight range of between 10 g/m$^2$ and 14 g/m$^2$.

17. A disposable article comprising:

a body, said body having a long axis, said body including an absorbent core for absorbing liquids, said absorbent core having a top side and a bottom side, a fluid-permeable topsheet positioned on said top side of said absorbent core, and a fluid-impermeable backsheet positioned on said bottom side of said absorbent core, said body having a pair of opposed side areas each terminating at a distal edge;

a pair of layered cuff assemblies, each of said pair of layered assemblies having a cuff standing portion and a cuff base portion, said cuff base portion being attached to one of said pair of opposed side areas whereby said cuff standing portion is in spaced apart relation from said distal edge of said body, each of said pair of layered cuff assemblies consisting of a first layer and a second layer, said second layer being layered nonuniformly on said first layer.

18. The disposable article of claim 17, wherein said first layer is continuous from said cuff standing portion to said distal edge of said body.

19. The disposable article of claim 17, wherein said first layer is composed of a nonwoven web of fibers.

20. The disposable article of claim 19, wherein said second layer is composed of a nonwoven web of fibers.

21. The disposable article of claim 17, wherein said first layer has a material weight and said second layer has a material weight, said weight of said first layer being about 14 g/m$^2$ and said weight of said second layer being in the range of between about 10 g/m$^2$ and 14 g/m$^2$.

22. In a body fluid absorptive article, said article including:

a longitudinal body, said body having a long axis, said body including an absorbent core consisting of a central crotch zone having two opposed sides extending outwardly from each side of said crotch zone, each of said sides having a distal edge defining a leg opening, said crotch zone defining means for positioning adjacent the crotch of the wearer to absorb body fluids, said absorbent core being composed of fluid-absorbent material, said body further including a fluid-permeable topsheet and a fluid-impermeable backsheet, said fluid-absorbent material of said absorbent core being disposed between said topsheet and said backsheet; and a pair of cuff assemblies, each of said pair of cuff assemblies including a cuff standing portion for fitting substantially within the groins of the wearer's crotch area and a cuff base portion for attachment to said longitudinal body, said cuff standing portion having a free end, each of said cuff assemblies having a first layer and a second layer, one of said layers extending from said free end of said cuff standing portion to said distal edge of said body, said second layer having a material weight, said material weight of said second layer being reduced proximate said free end of said cuff standing portion relative to the remainder of said cuff standing portion.

23. The body fluid absorptive article of claim 22, wherein said weight of said second layer proximate said free end of said cuff standing portion is between 1 g/m$^2$ and 4 g/m$^2$.

24. The body fluid absorptive article of claim 22, wherein said weight of said cuff standing portion other than proximate said free end of said cuff standing portion is between 10 g/m$^2$ and 14 g/m$^2$.

* * * * *